US006187828B1

(12) United States Patent
Woodrum et al.

(10) Patent No.: US 6,187,828 B1
(45) Date of Patent: Feb. 13, 2001

(54) CONTINUOUS PROCESS FOR MANUFACTURING SUPERABSORBENT POLYMER

(75) Inventors: G. Thomas Woodrum, Chesapeake; Monte Alan Peterson, Portsmouth, both of VA (US)

(73) Assignee: BASF Corporation, Mount Olive, NJ (US)

( * ) Notice: Under 35 U.S.C. 154(b), the term of this patent shall be extended for 0 days.

(21) Appl. No.: 09/199,020

(22) Filed: Nov. 24, 1998

(51) Int. Cl.[7] .......................................................... C08J 9/28
(52) U.S. Cl. ................................................ 521/64; 521/65
(58) Field of Search .......................................... 521/64, 65

(56) References Cited

U.S. PATENT DOCUMENTS

| | | |
|---|---|---|
| 4,857,610 | 8/1989 | Chmelir et al. . |
| 4,985,518 | 1/1991 | Alexander et al. . |
| 5,229,466 | 7/1993 | Brehm et al. . |
| 5,340,842 * | 8/1994 | Adamski et al. ....................... 521/64 |
| 5,500,451 * | 3/1996 | Goldman et al. ....................... 521/64 |
| 5,550,167 * | 8/1996 | Des Maris ............................. 521/64 |
| 5,563,179 * | 10/1996 | Stone et al. ............................ 521/64 |

OTHER PUBLICATIONS

Patent Abstract 4625001: Method for Continuous Production of Cross–Linked Polymer, 1993.

* cited by examiner

Primary Examiner—Morton Foelak
(74) Attorney, Agent, or Firm—David T. Banchik

(57) ABSTRACT

Disclosed herein is a continuous process to make super absorbing polymer characterized by feeding at the head-end of a pressurized vessel, an aqueous solution of SAP forming monomer solution, either in un-neutralized or pre-neutralized condition, the monomer(s) being conveyed to the reactor vessel at a relatively low temperature of from 5° C. to 15° C. into a pressurized head feed zone of the reactor. The head pressure is maintained the reactor at a minimum level of greater than or equal to about 20 p.s.i.g. and the SAP advances to the discharge end. A relatively constant mass of SAP is maintained of at least 50% volume of SAP in the vessel, and the rate of entry and exit are kept relatively constant. The reaction vessel is equipped with a venting means to regulate the internal bead pressure to advance the SAP to the discharge end without mechanical agitation. The continuous polymerization process is followed by drying and pulverizing the discharged SAP polymer, including optional post-treatment steps.

16 Claims, No Drawings

CONTINUOUS PROCESS FOR MANUFACTURING SUPERABSORBENT POLYMER

BACKGROUND OF THE INVENTION

The present invention is directed to a continuous process for making water-insoluble, crosslinked, high molecular weight polymers capable of absorbing and retaining large quantities of aqueous fluids (SAP). These polymers are well known in the art by various names such as superabsorbent polymers, hydrogels, hydrocolloids, and water absorbent hydrophilic polymers, etc. For the purpose of this description the term, "SAP" means superabsorbent polymer, collectively referring to such materials.

Exemplary superabsorbent polymers include crosslinked, partially neutralized polyacrylic acid (see U.S. Pat. No. 4,654,039); crosslinked, partially neutralized starch-acrylic acid graft polymer (U.S. Pat. No. 4,076,663); crosslinked, partially neutralized copolymer of isobutylene and maleic anhydride (U.S. Pat. No. 4,389,513); saponification product of vinyl acetate-acrylic acid copolymer (U.S. Pat. No. 4,124,748); hydrolyzate of acrylamide polymer or acrylamide copolymer (U.S. Pat. No. 3,959,569); or hydrolyzate of an acrylonitrile copolymer (U.S. Pat. No. 3,935,099). The teachings of the above patents as embodiments of superabsorbent materials are hereby incorporated by reference.

Superabsorbent polymers find use in many fluid absorption applications with the primary use being in the field of personal care products such as diapers, sanitary napkins, adult incontinent products, absorption pads for medical uses, etc. The largest market for superabsorbent polymers is found in disposable diapers for infants; see e.g. U.S. Pat. Nos. 3,669,103; 3,670,731 or 4,654,039.

Numerous other patents disclose superabsorbent polymers and their uses, such as U.S. Pat. No. 4,076,663; 4,552,938; 4,507,438; 4,5235,098; 4,820,773 and European Patent Application 189,163.

U.S. Pat. No. 4,985,518 discloses a method of preparing a solid water absorbing resin including mixing a monomer solution of (A) acrylic acid neutralized 70–100 mole percent; and (B) a water-miscible to water-soluble polyvinyl monomer in a combined concentration of up to about 50 wt. %; with water to form a mixed monomer solution, and adding a thermal initiator and a redox initiator to the mixed monomer solution to form an initiated mixed monomer solution at a temperature below the decomposition temperature of the thermal initiator. The addition of the redox initiator thereto and polymerization of the monomers causes a rise in the temperature of the initiated mixed monomer solution to a level sufficient to activate the thermal initiator.

U.S. Pat. No. 4,857,610 assigned to Stockhausen, discloses a moving conveyor apparatus for the continuous production of SAP and copolymers of water-soluble monomers particularly acrylic acid and/or methacrylic acid at up to about 40% monomer solids. The trough-like shape of the conveyor belt changes continuously into an extended flat profile during the polymerization process; starting from the side edges and working towards the center of the trough formed by the conveyor belt. The resulting polymer gel strand is released continuously during the transition of the curved trough-like shape of the conveyor belt into the extended, flat form.

U.S. Pat. No. 4,625,001 assigned to Nippon Shokubai discloses a continuous process to make SAP comprising the steps of continuously feeding an aqueous solution of a SAP forming monomer in aqueous solution to effect polymerization into a water-containing cross-linked polymer along with a polymerization initiator. The vessel is provided with a plurality of mutually parallel rotary stirring shafts each fitted with stirring blades. The process includes finely dividing a water-containing gel polymer issuing from the polymerization in progress by the shearing force of stirring blades generated by the rotation of said stirring shafts while allowing the radical aqueous solution polymerization to proceed without interruption, and continuously discharging the resultant finely divided water-containing gel polymer out of said vessel.

Among the known batch processes for making SAP, there is the aqueous solution batch process at relatively low monomer solids (about 30 solids) coupled to drum-type dryers; there is the aqueous solution batch process coupled to a tunnel-type dryer. The aforementioned processes represent a significant capital cost per unit of SAP produced.

A continuous process has been discovered for use with a variety of reaction vessel shapes which avoids polymerization on a moving conveyor, and the need for agitation equipment thereby providing greater simplicity and ease of operation with relatively low capital cost per unit of SAP produced.

SUMMARY OF INVENTION

This invention is directed to a continuous process for manufacturing superabsorbent polymers in a pressurized, unagitated reaction vessel, the vessel is preferably elongated and vertically oriented. The process is characterized in the beginning by feeding a cold mixture of monomer, initiator and water to the vessel which is at least half full of SAP. The vessel is under pressure, and a head pressure at the inlet end is maintained at a level sufficient to advance the SAP toward the discharge outlet. The SAP forming monomer mixture is charged to the inlet of the vessel at a rate that is kept substantially equal to the rate of discharge of SAP through the outlet of the vessel. The process maintains an essentially constant mass of monomer/SAP in the vessel and the residence time is maintained to obtain a desired high level of monomer conversion. The SAP reaction mass advances in a laminar-like flow without agitation and conditions are maintained so as to minimize breakthrough of gas and/or liquid to the outlet where at least 50% of the vessel volume contains the mass of SAP, preferably at least 75% by volume, and most preferably about 90% by volume SAP is maintained during steady state conditions.

The process is also characterized by a positive temperature gradient in the direction of the advancing polymer, rising to a peak temperature nearer to the discharge (tail) end. The pressure in the vessel is maintained to achieve an efficient polymer discharge rate. The advancing polymer moves with gravity and pressure without mechanical assistance or agitation.

Therefore the continuous process of the invention is characterized by the simultaneous feeding at the head-end of an aqueous solution of SAP forming monomer solution, either in un-neutralized or pre-neutralized condition, the monomer(s) being conveyed to the reactor vessel at a relatively low temperature, preferably from 5° C. to 15° C. The head pressure in the gas space of the feed zone above the SAP mass is maintained at a minimum level of greater than or equal to about 20 p.s.i.g., and is adjusted to provide a means to continuously advance the SAP polymer toward the discharge. The monomer feed solution is preferably kept under an intermittent or continuous inert gas purge, such as with nitrogen. The reaction vessel is equipped with a venting means to regulate the internal head pressure. The continuous polymerization process is followed by steps typically involving drying and pulverizing the discharged SAP polymer, as well as optional post-treatment steps specified hereinbelow. The volume percent SAP maintained in the vessel is preferably from 75%–95% of the volume capacity of the vessel. Most preferably, about 90 volume % of SAP is maintained in the vessel during the continuous process.

The preferred process of this invention comprises continuously feeding an aqueous monomer solution comprising at greater than or equal to about 20%, preferably greater than or equal to 28% and, up to 46% SAP forming monomer content, a cross-linking monomer, and initiator(s). The monomer feed solution passes a zone having an inert gas purge, and is initiated as it enters the reaction vessel. As the charged and initiated monomer feed solution advances toward the discharge end, the temperature increases as polymer conversion occurs. The continuous process is therefore preferably conducted under adiabatic conditions. The preferred temperature gradient in the advancing polymerizate and the preferred extent of conversion of monomer to polymer is such that the free monomer content in the discharging SAP gel can be kept within a desired tolerance limit, such as less than 3500 ppm of residual monomer.

In a preferred embodiment of the process, wherein the monomer(s) fed to the vessel is not pre-neutralized, the discharged polymer can be treated by neutralizing preferably 60 to 80 percent of the acid groups where present, drying the polymer to a moisture content below about 5 weight percent, and pulverizing the dried polymer to a powder. The preferred dried powder is subsequently surface-crosslinked by applying a secondary crosslinker to the particles.

Superabsorbent polymers continuously prepared according to the invention comprise lightly crosslinked aqueous gel-forming polymer from ethylenically unsaturated monomer or alkali metal salt of such monomers or mixtures thereof and one or more types of crosslinking agents.

The process herein utilizes a major amount (>20%) of a superabsorbent polymer (SAP) forming monomer, optionally with a minor amount of other copolymerizable modifying monomers and/or crosslinker, known and used in the art. Preferably the SAP forming monomer which is ethylenically unsaturated is water soluble. Exemplary water soluble, SAP forming monomers are those containing carboxyl groups, carboxylic acid anhydride groups, carboxylic acid salt groups, sulfonic acid groups, sulfonic acid salt groups, hydroxyl groups, amide groups, amino groups and quaternary ammonium salt groups. Examples of polymerizable groups for the SAP forming monomer are acrylic groups, methacrylic groups, allyl groups and vinyl groups. An extensive listing of suitable SAP forming monomers is found in U.S. Pat. No. 4,076,663 at col. 2, lines 6–68 and col. 3, lines 1–12; the teachings of which are hereby incorporated by reference. The most preferred monomer used to make the superabsorbent polymer continuously in accordance with the invention is acrylic acid.

It has been found that the continuous process according to the invention is adaptable to either the pre-neutralized monomer method or the post-neutralization method, as these are known in the art. In the preferred embodiment wherein the SAP forming monomer contains carboxylic acid groups, the monomer may be neutralized to any extent prior to polymerization or the monomer may be polymerized without neutralizing, and the SAP polymer may be neutralized subsequent to polymerization with a base such as alkali metal hydroxide, e.g. sodium or potassium hydroxide, or a compound such as ammonium hydroxide.

The term crosslinker can refer to "internal crosslinkers" or external crosslinkers. Internal crosslinkers mean crosslinkers which are present during the polymerization reaction in the reaction vessel giving rise to a crosslinked SAP polymer. Internal crosslinker monomers as well as crosslinking polymers can be used as internal crosslinkers. Polymeric internal crosslinkers include polyacrylic esters of polyols, polymethacrylic esters of polyols, polyallyl amines, polyally ethers, polyacrylamido compounds, polymethacrylamido compounds and divinyl-compounds. The internal crosslinker is preferably at least partially soluble in water or in the SAP forming monomer solution. The preferred internal crosslinkers are monomeric. Preferred monomeric internal crosslinkers are those which contain at least two groups reactive with the SAP forming monomer or polymer, such as those which contain allylic groups. Specific examples of cross-linking monomers that can be present during polymerization are tetraallyloxyethane, N,N'-methylene bisacrylamide, N,N'-methylene bismethacrylamide, triallylamine, trimethylol propane triacrylate, glycerol propoxy triacrylate, divinyl benzene and the like. A most preferred monomeric internal crosslinker is pentaerythritol triallyl ether (P-30) available from Daiso Co., Ltd, Japan.

The term "surface crosslinker" or "post-crosslinker" is defined herein to mean a crosslinking, which is effected after polymerization. The distribution of the surface crosslinker can be any distribution throughout the SAP polymer particles, but is typically and preferably concentrated in a region of the polymer whether inside the polymer mass or at or near the surface of the solid polymer mass. The prevailing practice in the art is to utilize a surface crosslinker by locating the concentration toward the surface of the polymer particle mass when effectuating the post-crosslinking reaction. This is done preferably after milling the SAP into particles and achieves improved performance properties for the SAP. Known surface crosslinking techniques provide polymers having improved performance properties such as the reduction of the tendency of the particles to gel block and agglomerate when wetted with aqueous liquid. Gel blocking is a well known phenomenon.

Known methods for post-polymerization crosslinking include, U.S. Pat. No. 4,666,983 using a difunctional crosslinking agent without any carrier solvent, such as polyhydric alcohols, polyglycidyl ethers, polyfunctional amines and polyfunctional isocyanates. U.S. Pat. Nos. 4,507,438 and 4,541,871, incorporated by reference, illustrate the use of a difunctional compound in water with inert solvent or mixture of solvents. The difunctional compounds include glycidyl ethers, haloepoxies, aldehydes and isocyanates. The solvents include polyhydric alcohols with ethylene glycol, propylene glycol and glycerin enumerated as preferred polyhydric alcohols. U.S. Pat. No. 5,140,076 teaches a water-solvent-crosslinker mixture. Crosslinkers such as polyhydric alcohol, diglycidyl ether, polyarizidene, urea, amine and ionic crosslinkers are suggested. EPO 0 509,708 discloses the use of a polyhydroxy compound in a water based coating solution which may contain a nonionic surfactant and optionally a water-soluble solvent. U.S. Pat. No. 5,002,986 discloses agglomerating and surface crosslinking fine (<300 microns) superabsorbent particles. Other patents, which have described the surface crosslinking of superabsorbent polymers, are U.S. Pat. No. 4,666,975 U.S. Pat. Nos. 3,202,731; 4,043,952; 4,127,944; 4,159,260; 4,251,643; 4,272,514; 4,289,814; 4,295,987; 4,500,670; 4,587,308; 4,732,968; 4,735,987; 4,755,560; 4,755,562; 4,758,617; 4,771,105; 4,820,773; 4,824,901;4,954,562; 4,973,632; 4,985,518; 5,026,800, each of which are incorporated by reference.

In an alternative embodiment the monomer may also be polymerized in the presence of a preformed polymer to produce a grafted SAP polymer. Optional, grafting polymer components used in making graft polymer embodiments are water-soluble hydroxy containing polymers, such as polysaccharides and vinyl or acrylic polymers. Examples of water soluble polysaccharides are starches, water soluble celluloses and polygalactommans.

In preparing the preferred superabsorbent polymer of this invention, the SAP forming monomer and the optional water soluble grafting polymer are typically charged at about 20 to about 50 weight percent monomer concentration. The amount of polyethylenically unsaturated internal crosslinking monomer will vary from about 0.0005 to about 1.0 mole percent based on the moles of acrylic acid, and preferably about 0.01 to about 0.3 mole percent.

The preferred polymerization initiators suitably used in this invention are redox initiators. Photoinitiators could be used but are not preferred.

Additionally, thermal initiators are selected to conduct the continuous process in such a manner so as to achieve a residual monomer level less than 2000 ppm by weight. The working embodiments provide a useful guideline as to the types and amounts of initiator used to practice the invention.

Referring to the redox initiators, any of the well known water soluble reducing agents and oxidizing agents can be used in this invention. Examples of reducing agents include such compounds as ascorbic acid, alkali metal sulfites, alkali metal bisulfites, ammonium sulfite, ammonium bisulfite, alkali metal hydrogen sulfite, ammonium hydrogen sulfite ferrous metal salts, e.g., ferrous sulfates, and the like.

Oxidizing agents include such compounds as hydrogen peroxide, alkali metal persulfate, ammonium persulfate, alkylhydroperoxides, peresters, diacyl peroxides, silver salts, and the like. A particularly preferred redox initiator pair is ascorbic acid and hydrogen peroxide.

In the use of a redox initiator, in order to obtain a consistent, steady state in this invention, the amount of the reducing agent should be between about $2 \times 10^{-9}$ to about $2.0 \times 10^{-4}$ mole percent based on moles of SAP forming monomer(s) used. The amount of oxidizing agent used will vary from about $2.0 \times 10^{-6}$ to about 1.1 mole percent, based on moles of SAP forming monomer used. By this amount, initiation commences as the solution enters the vessel.

Useful thermal initiators are the azo initiators, i.e., compounds which contain the —N=N— structure. Any of the azo compounds which have some solubility in water or in an acrylic acid-water mixture and which have a 10 hour half life at 30° C. or above can be used. Example of useful azo initiators are 2,2'-azobis (amidino propane) dihydrochloride, 4,4'-azobis (cyanovaleric acid), 4,4'-butylazo-cyanovaleric acid, 2,2'-azobis (isobutyronitrile), and the like. A preferred azo initiator for use in this invention is 2,2'-azobis (amidinopropane) dihydrochloride. A sugested amount of thermal initiators is from $6.0 \times 10^{-8}$ to about $6.0 \times 10^{-4}$ mole percent based on the weight of SAP forming monomer(s). The most preferred thermal initiators are those used in the examples below.

The polymerization process for preparing the compositions of this invention is conducted in water at a SAP forming monomer concentration of from 20% to 46%. based on the total weight of water and SAP forming monomer. At lower concentrations, reaction productivity is undesirably low while at higher solids level, temperature control becomes more difficult and the risk of catastrophic solidification of the polymer mass increases, as it is known particularly in the polymerization of acrylic acid in solution.

Surprisingly, it was found that the monomer feed stream did not boil in this range of monomer concentration at a reactor pressure suitable for polymer gel discharge. The pressure range found suitable for a reaction zone having a L/D of 3 to 1 is in a range of 20–50 p.s.i.g., (1.3 to 3.3 bar) and a monomer feed temperature of about 50° F. The temperature of the gel nearest the discharge location is approximately 300° F.

Under the post-neutralization method, carboxylic acid groups of the SAP are neutralized with a base in the amount of about 50 to about 100 mole percent, preferably about 65 to about 75 mole percent. The preferred bases are the alkali metal hydroxides with the most preferred base being sodium hydroxide. Other bases, such as alkaline earth metal hydroxides, ammonium hydroxide, alkali metal, alkaline earth metal and ammonium carbonates, bicarbonates, amines and the like can also be used.

As stated hereinbefore, the polymerization reaction is an adiabatic reaction conducted without the application of external heat. The monomers, i.e., acrylic acid, the cross-linking monomer and the polysaccharide, if used, are dissolved in water and charged to the reactor vessel, which contains hot SAP. The temperature is lowered to about 5° C. to about 20° C. prior to introducing into the reaction vessel. The polymerization initiators, i.e., the thermal initiator, if used, the reducing agent and the oxidizing agent are added to the reactor with thorough mixing. Dissolved oxygen is removed by a nitrogen cocurrent strip of the feed solution as it is introduced into the reactor. Upon contact of the monomer mixture with the SAP polymerization begins as indicated by a rise in temperature of the charged mixture. Monomer mixture is added while SAP polymer is discharged from the reaction vessel. Peak temperatures are usually reached in about 1 to 3 hours. Generally, the peak temperature will be about 60° C. to about 75° C. As the SAP advances in the reaction vessel, the peak temperature is reached and conversion of monomer is sufficient at the point of discharge such that the residual monomer content can be kept below a level, generally in the range of 1000–5000 ppm. The total residence time can be maintained in a range of from 3 to 6 hours.

When the polymerizate is discharged as polymer gel it is chopped into small particles. In the post-neutralized method, an aqueous base is then added to neutralize some or all of the acid groups. The gel is again chopped to ensure uniform mixing of the base with the polymer. The polymer is dried to a moisture content of less than about 5 weight percent. The dried polymer is then ground and sieved to a particle size of about 20 to about 400 mesh U.S. Standard Sieve, with a preferred range of 20–200 mesh, and most preferably 95 percent of said particles are between 20 and 140 mesh.

Test Methods

The following test methods were used to determine the properties of the superabsorbent polymers described herein.

Absorbency Under Load (AL) at 0.3 pi

This test is designed to determine the absorbency under load of a superabsorbent material. The amount of saline (0.9% wt/% sodium chloride solution) absorbed with the weight applied to the polymer indicates the effectiveness of the polymers absorbency in a diaper system under the weight of a baby.

Absorbency under load is measured using a plastic petri dish with elevating rods and a 1.241"OD×0.998"ID×1.316" long plexiglass tube with a wire net (100 mesh) at the bottom of the tube. The particle size of the test samples is between 30 to 50 mesh, (through 30 and retained on 50).

A test sample, 0.160±0.01 g is weighed out and recorded as $S_1$. The sample is placed in the plastic tube and is spread evenly over the wire net. A 100 g weight and a disc are placed on the sample. The assembly (polymer sample, tube, disc and weight) is weighed and recorded as $W_1$. The assembly is then placed in a petri dish containing 40 ml 0.9% saline aqueous solution. After one hour of absorption, the assembly is removed from petri dish and excess saline blotted from the bottom. The assembly is weighed again and this value recorded as $W_2$. Absorbency under load (AUL) is equal to $(W_2-W_1)/S_1$ and is express in g/g.

Absorbency Under Load (AUL) at 0.6 and 0.9 psi

The absorbency under load at 0.6 psi is determined in the same manner as the above described absorbency under load at 0.3 psi except a 200 gram weight is used instead of the 100 gram weight. The absorbency under load at 0.9 psi is determined in the same manner as above except a 300 gram weight is used.

Centrifuge Retention Capacity (CRET)

This test is designed to measure the amount of saline solution retained inside a superabsorbent polymer when under a specific centrifuge force.

Approximately 0.200 grams of superabsorbent polymer are placed into a sealable tea bag (7.5 cm×6.5 cm) and the tea bag sealed. The tea bag and polymer are immersed in a 0.9% saline solution for 30 minutes and then centrifuged for three minutes at 1600 rpm on a 21.6 cm diameter centrifuge. The weight difference before centrifuging and after is the amount of saline solution absorbed by polymer gel which is divided by original dry polymer weight and this value is the centrifuge retention capacity of the polymer expressed in g/g.

The following examples illustrate working embodiments of the invention. Parts and percentages, unless otherwise designated, are parts and percentages by weight. These examples are intended to be illustrative and are not intended to limit the scope of the invention or the claims.

EXAMPLE 1

A vertically oriented reactor having a nominal working capacity of 200 liters and an aspect ratio of 3/1 is used in this example. The reactor contains no internal components such as baffling or agitation. The reactor is insulated to maintain the temperature developed during the course of operation. Previous experimentation has left a 90% residual volume of SAP polymer in the reactor, which is the required starting condition for running continuously. The top or head of the reactor is configured with valved opening or ports to 1) enable reactant feeds to be added on a continuous basis, 2) stripped oxygen to be vented continuously, and 3) the mounting of temperature and pressure measuring devices to monitor processing conditions. The bottom of the reactor is configured with a double discharge screw to continuously remove the reacted polymer. In this example there are three reactant components that will be metered into the reactor on a continuous basis. The reactants are combined into a common junction point just prior to entering into the reactor. Additionally, nitrogen is added at this junction point to facilitate removal of dissolved oxygen contained in the reactant feeds. The reactant feeds are 1) monomer feed, consisting of acrylic acid, pentaerythritol triallyl ether crosslinker, and deionized water, 2) hydrogen peroxide and deionized water, and 3) ascorbic acid, V-50 (Wako) and deionized water. The hydrogen peroxide and ascorbic acid function as a redox initiation couple. For this case the monomer concentration is prepared to achieve a 32% acrylic acid concentration in the reactor. In this example, a reactant residence time of 3 hours was selected. The three reactant components are metered into the reactor at a temperature of 10±2° C. and at a feed rate to achieve the required residence time. Simultaneously with the beginning of the addition of reactants to the reactor, polymer is removed by the discharge screw at an equivalent rate. Process control (i.e. residence time) is maintained by controlling the polymer level in the reactor at 90% (180 liters) of the working capacity of the reactor. This is achieved by a load cell upon which the reactor is mounted. Similarly, oxygen removed by the nitrogen stripping is removed from the vapor zone in the top of the reactor. Pressure control is maintained at 3.4 bars. As pressure exceeds 3.4 bars, the pressure is vented to remove the oxygen containing vapors. The 3.4 bar pressure in this example is sufficient to advance the polymer toward the discharge screw.

Polymer removed from the reactor had an absorbency of 32.2 g/g as measured by the Centrifuge Retention test method. This polymer was subsequently surfaced crosslinked and was retested and found to have a 27.0 gig Centrifuge Retention and a 24.0 gig 0.9 Absorbency Under Load (0.9 AUL).

EXAMPLE 2

A vertically oriented reactor having a nominal working capacity of 200 liters and an aspect ration of 3/1 is used in this example. The reactor contains no internal components such as baffling or agitation. The reactor is insulated to maintain the temperature developed during the course of operation. Previous experimentation has left an 80% residual volume of polymer in the reactor, which is within the required starting range for running continuously. The top of the head of the reactor is configured with valved openings or ports to 1) enable reactant feeds to be added on a continuous basis, 2) stripped oxygen to be vented continuously, and 3) the mounting of temperature and pressure measuring devices to monitor processing conditions. The bottom of the reactor is configured with a double discharge screw to continuously remove reacted polymer. In this example there are three reactant components that will be metered into the reactor on a continuous basis. The reactants are combined into a common junction point just prior to entering the reactor. Additionally, nitrogen is added at the junction point to facilitate removal of dissolved oxygen contained in the reactant feeds. The reactant feeds are 1) monomer feed consisting of acrylic acid and pentaerythritol triallyl ether, a crosslinker, and deionized water, 2) hydrogen peroxide and deionized water, and 3) ascorbic acid, V-50, a thermal initiator and deionized water. The hydrogen peroxide and ascorbic acid function as a redox initiation couple. In this case the monomer concentration is prepared to achieve a 46% acrylic acid concentrate in the reactor. In this example, a reactant residence time of 3 hours was selected. The three reactant components are metered into the reactor at a temperature of 10±2° C. and at a feed rate to achieve the required residence time. Simultaneously with the beginning of the addition of reactants to the reactor, polymer is removed by the discharge screw at a rate equivalent to the rate of monomer addition. Process control (i.e. residence time) is maintained by controlling the polymer in the reactor at 80% (160 liters) of the working capacity of the reactor. This is achieved by a load cell upon which the reactor is mounted. Similarly, oxygen removed by the nitrogen stripping is removed from the vapor zone in the top of the reactor. Pressure control is maintained at 3.4 bars. As pressure exceeds 3.4 bars, the pressure is vented to remove oxygen containing vapor. Polymer removed from the reactor had an absorbency of 28.6 g/g as measured by the Centrifuge Retention test method. This polymer was subsequently surfaced crosslinked and was retested and found to have 24.9 g/g Centrifuge Retention and a 20.0 gig 0.6 Absorbency Under Load (0.6 AUL).

EXAMPLE 3

A vertically oriented reactor having a nominal working capacity of 200 liters and an aspect ratio of 3/1 is used in this example. The reactor contains no internal components such as baffling or agitation. The reactor is insulated to maintain the temperature developed during the course of operation. Previous experimentation has left an 90% residual volume of polymer in the reactor, which is the required starting condition for running continuously. The top or head of the reactor is configured with valved openings or ports to 1) enable reactant feeds to be added on a continuous basis, 2) stripped oxygen to be vented continuously, and 3) the mounting of temperature and pressure measuring devices to monitor processing conditions. The bottom of the reactor is configured with a double discharge screw to continuously remove reacted polymer. In this example there are three reactant components that will be metered into the reactor on a continuous basis. The reactants are combined into a common junction point just prior to entering the reactor. Additionally, nitrogen is added at the junction point to facilitate removal of dissolved oxygen contained in the reactant feeds. The reactant feeds are 1) monomer feed consisting of acrylic acid neutralized with sodium hydroxide to a molar percentage of 75, pentaerythritol triallyl ether, a crosslinker, and deionized water, 2) hydrogen peroxide and deionized water, and 3) ascorbic acid, V-50, a thermal initiator and deionized water. The hydrogen peroxide and ascorbic acid function as a redox initiation couple. In this case the monomer concentrate is prepared to achieve a 28% acrylic acid concentration in the reactor. In this example, a reactant residence time of 6 hours was selected. The three reactant components are metered into the reactor at a temperature of 10±2° C. and at a feed rate to achieve the required residence time. Simultaneously with the beginning of the addition of reactants to the reactor, polymer is removed by the discharge screw at a rate equivalent to the rate of monomer addition. Process control (i.e. residence time) is maintained by controlling the polymer in the reactor at 90% (180 liters) of the working capacity of the reactor. This is achieved by a load cell upon which the reactor is mounted, Similarly, oxygen removed by the nitrogen stripping is removed from the vapor zone in the top of the reactor. Pressure control is maintained at 3.4 bars. As pressure exceeds 3.4 bars, the pressure is vented to remove oxygen containing vapor.

Polymer removed from reactor had an absorbency of 37.3 g/g as measured by the Centrifuge Retention test method. This polymer was subsequently surfaced crosslinked and was retested and found to have a 30.1 g/g Centrifuge Retention and a 15.3 g/g 0.9 Absorbency Under Load (0.9 AUL).

We claim:

1. A continuous process for making superabsorbent polymer, comprising adding a cold mixture of super absorbing polymer-forming monomer, initiator, crosslinker and water under pressure to an inlet zone of a reaction vessel, said vessel containing at least 50% of it's volume capacity of super absorber polymer (SAP), polymerizing said monomer to SAP while maintaining said inlet zone under sufficient pressure to advance the SAP without agitation, advancing the SAP toward a discharge zone, discharging SAP at a discharge point in said vessel at a rate approximately equal to the rate of addition of said cold mixture so as to maintain said vessel at least 50% full of SAP.

2. The process of claim 1 wherein said cold mixture added to said vessel contains from 28% to 46% solids content.

3. The process of claim 1 wherein said super absorbing polymer-forming monomer contains functional groups selected from the group consisting of carboxyl groups, carboxylic acid anhydride groups, carboxylic acid salt groups, sulfonic acid groups, sulfonic acid salt groups, hydroxyl groups, amide groups, amino groups and quaternary ammonium salt groups.

4. The process of claim 2 wherein said super absorbing polymer-forming monomer contains repeating units selected from acrylic groups, methacrylic groups, allyl groups and vinyl groups.

5. The process of claim 1 further comprising the step of post-crosslinking.

6. The process of claim 1 wherein said super absorbing polymer-forming monomer is neutralized prior to polymerizing.

7. The process of claim 1 wherein said SAP is neutralized after polymerization.

8. The process of claim 1 wherein the temperature of said cold mixture as it enters said vessel is from 50 to 15° C.

9. The process of claim 1 wherein the pressure is maintained at from about 20 to 50 p.s.i.g. .

10. The process of claim 1 wherein said vessel is teflon-lined.

11. The process of claim 1 wherein said vessel is constructed of 316 stainless steel.

12. An absorbent article comprising the product of claim 1.

13. The article of claim 12 comprising a diaper and the product of claim 1 distributed in a layer.

14. The article of claim 12 further comprising pulp fluff evenly dispersed with the product of claim 1.

15. A method of use for the product of claim 1 as a component in an absorbent core of a diaper, comprising incorporating said product into a nonwoven composite and assembling said diaper with said composite containing the product of claim 1.

16. A method of use of the product of claim 1 for underwater cable, comprising extruding said product in an advancing cable assembly.

* * * * *